United States Patent [19]
Mader et al.

[11] Patent Number: 5,284,759
[45] Date of Patent: Feb. 8, 1994

[54] BIOLOGICAL PRODUCTION OF ACETAL OR KETAL SUBSTITUTED BENZENE COMPOUNDS

[75] Inventors: Roger A. Mader, Stillwater; Kestutis J. Tautvydas, Lake Elmo, both of Minn.

[73] Assignee: Minnesota Mining and Manufacturing Company, St. Paul, Minn.

[21] Appl. No.: 931,017

[22] Filed: Aug. 17, 1992

Related U.S. Application Data

[63] Continuation of Ser. No. 359,106, May 31, 1989, abandoned.

[51] Int. Cl.$^5$ .................. C12P 17/06; C12P 17/04; C12P 7/26; C12N 9/02
[52] U.S. Cl. .................. 435/125; 435/126; 435/148; 435/189
[58] Field of Search ............ 435/125, 126, 156, 155, 435/146, 189, 148

[56] References Cited

U.S. PATENT DOCUMENTS 4,927,759  5/1990  Schofield .................. 435/156

OTHER PUBLICATIONS

Catelani, D., "Metabolism of Biphenyl", *Biochem. J.*, 134, pp. 1066, 1973.
Gibson et al., "Initial Reactions in the Oxidation of Ethylbenzene by *Pseudomonas putida*", *Biochemistry*, vol. 12, No. 8, pp. 1526-1527, 1973.
Yeh, W. et al., "Toluene Dioxyginase: A Multicomponent Enzyme System", *Biochem. and Biophys. Res. Comm.*, vol. 78, No. 1, pp. 401-410, 1977.
Subramamian, V. et al., "Double Hydroxylation Reactions in Microorganisms", *J. Indian Inst. Sci.*, vol. 60, No. 8, pp. 143-148, 1978.
Klecka, G. M. et al. "Metabolism of Dibenzo-p-Dioxin and Chlorinated Dibenzo-p-Dioxins by a *Beijerinckia* species", Appl. and Environ. Microbiology, vol. 39, No. 2, pp. 288-296, 1980.
Griffin, M. et al. "Possible Uses of Microorganisms in the Manufacture of Plastics and Synthetic Fibers", *Biotechnology* and *Genetic Engineering Reviews*, vol. 4, pp. 263-290, 1986.

*Primary Examiner*—Marian Knode
*Attorney, Agent, or Firm*—Gary L. Griswold; Walter N. Kirn; Paul W. Busse

[57] ABSTRACT

Meta-hydroxyphenylacetylenes are produced from phenyl-substituted ketal or acetal precursors. Using biotransformation processes, these precursors serve as substrates that are converted to cis-dihydrodiol intermediates. The cis-dihydrodiols can be converted chemically to the corresponding meta-substituted compounds, e.g., meta-substituted phenols, and then to m-hydroxyphenylacetylene, which is an intermediate needed to produce acetylene-terminated resins. The biotransformation step employs arene-2,3-dioxygenase in intra- or extra- cellular form.

9 Claims, No Drawings

BIOLOGICAL PRODUCTION OF ACETAL OR KETAL SUBSTITUTED BENZENE COMPOUNDS

This invention was made with Government support under F49620-88-C-0032 awarded by the Air Force. The Government has certain rights in this invention.

BACKGROUND OF THE INVENTION

This is a continuation of application Ser. No. 07/359,106, filed May 31, 1989, now abandoned.

1. Field of the Invention

This invention relates to the production of meta-substituted phenols using biotransformation processes, and includes novel cyclohexadienediols.

2. Description of the Related Art

Acetylene-terminated resin (AT resin) systems consist of molecules with terminal acetylene groups that form highly crosslinked network structures during a thermosetting cure reaction. The backbone of the resin molecules can be tailored with various chemical structures and variable chain length. AT resins have been prepared with backbone structures tailored to provide long term use ranging from 250° to 550° F. (121° to 288° C.), and short term use ranging from 600° to 650° F. (316° to 343° C.). Some of the backbone molecules that have been used with good results include isopropylidenediphenol, diphenylsulfone, and quinoxalines. AT resins are described by F. E. Arnold in *Current and Future Chemistry of Aerospace Organic Matrix Resins*, Proceedings of the American Society for Composites (August 1987), the disclosure of which is incorporated herein by reference. AT resins are also described by P. M. Hergerrother, *American Chem. Soc., Prep. Polymer Division*, 25(1):97 (1984). Outstanding properties of AT resins are their extremely low moisture uptake (less than 0.06%), absence of volatiles during cure, and excellent mechanical stability at high temperatures.

A key chemical intermediate needed to make AT resins is meta-hydroxyphenylacetylene (m-HPA). Unfortunately, the current high cost for the chemical synthesis of this intermediate has inhibited further development of AT resins. This intermediate was available only through chemical processes until the present invention. Chemically synthesized AT resins on the market today include an AT imide, MC-600, and an AT isoamide, IP-600, made by National Starch and Chemical Co.

The use of biotransformation reactions to effect syntheses is not new. Fermentations, in particular, have been used for centuries to make beverages. Over the last 50 years, microorganisms have been used commercially to make compounds such as antibiotics, vitamins, and amino acids. However, their use for making industrial specialty chemicals has been much less widespread. It has been realized only recently that microbes may be able to provide an economical route to certain compounds that are difficult or costly to make by conventional chemical means.

In the last 20 years or so a number of publications have appeared describing "biotransformations", or biochemical conversion reactions performed by microorganisms. Of interest to the present work, publications on the bio-oxidation of hydrocarbons, particularly petroleum-based aromatics, have appeared. D. T. Gibson (in "Fate and Effects of Petroleum Hydrocarbons", Ed. D. A. Wolf, Pergamon Press, New York, 1977) describes the oxidation of benzene and similar aromatic substances by microorganisms. Of particular interest here is the oxidation of certain aromatic molecules to cis-2,3-dihydrodiol derivatives. For example, toluene can be oxidized to a cis-2,3-dihydrodiol, as an intermediate in a series of oxidation products, using certain strains of the species *Pseudomonas putida*. In the pathway below, $E_1$ is an arene 2,3-dioxygenase enzyme that converts a substituted benzene to a corresponding cis-dihydrodiol. The second enzyme, $E_2$ is a dihydrodiol dehydrogenase, that forms a catechol. The next enzyme of the pathway, $E_3$ is a catechol dioxygenase, which oxygenates and opens the aromatic ring itself, thereby forming a 2-oxoacid.

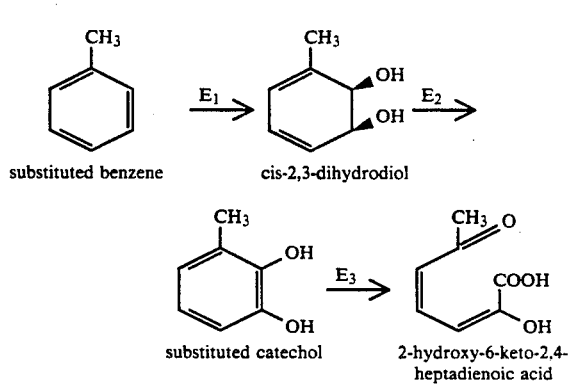

substituted benzene     cis-2,3-dihydrodiol substituted catechol     2-hydroxy-6-keto-2,4-heptadienoic acid Gibson et al. have published on the oxidative degradation of a number of aromatic molecules by microorganisms (see, e.g., *Biochemistry*, 7(7):2653 (1968). idem 9(7):1626(1970), *J. Bacteriol.*, 119(3):930 (1974)). Gibson et al., in *Biochemistry*, 7(11):3795 (1968), describe the formation of 4-chloro-2,3-dihydroxy-1-methyl cyclohexa-4,6-diene by *P. putida* from the substrate p-chlorotoluene and its subsequent acid-catalyzed dehydration to 3-chloro-6-methylphenol.

Other exemplary publications include T. Hudlicky et al., (*J. Am. Chem. Soc.*, 110:4735(1988)) describing syntheses through microbial oxidations; H. L. Holland and B. Munoz (*Can. Chem.*, 66:2299(1988)) describing the oxidation of sulfides to sulfones by fungi; and R. Csuk and B. I. Glanzer (*Z. Naturforsch. B.*, 43:1355(1988)) describing the enzymatic deacetylation of laevoglucosan triacetate to deacetylated derivatives.

In the patent literature, G. S. Fonken (U.S. Pat. No. 3,392,171 to The Upjohn Company) illustrates the oxygenating activity of certain microorganisms by disclosing the oxidation of a wide range of bicyclohexyl compounds to hydroxy or keto derivatives, using a number of microorganisms of Phylum III, Subphylum 2. S. Hagedorn (U.S. Pat. No. 4,634,668 to Celanese Corporation) discloses the oxidation of pars-xylene to paracresol through a dihydroxy intermediate made by biotransformation using *Pseudomonas putida* Biotype A strain ATCC 39119, followed by acid treatment. In U.S. Pat. Nos. 4,673,646 and 4,666,841 the same inventor and assignee disclose the conversion of toluene or substituted toluenes to 2-hydroxymuconicsemialdehyde and its substituted derivatives, and their conversion to picolinic acid and pyridine products. P. C. Maxwell (U.S. Pat. No. 4,731,328 to Celgene Corporation) discloses the oxidation of substrates such as toluene and catechol to muconic acid, which can be further reacted to give adipic acid which is useful in the plastics industry. It describes the microorganism which performs this biotransformation (ATCC No. 31916 strain of *Pseudomonas putida* Biotype A.), the culture and the media.

Ketals and acetals can be prepared by methods known in the art, see,. e.g., *Survey of organic Syntheses*, C. A. Buehler and D. E. Pearson, Vol. 1, (1970), the disclosure of which is incorporated herein by reference.

Furthermore "cyclic ketals" of the general formula:

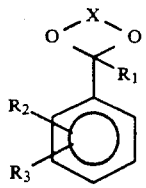

where $R_1$, $R_2$, $R_3$, and X are as defined therein, were described or use in sunscreens by Moller et al in German Patent 2526312. That patent, the disclosure of which is incorporated herein by reference, describes generally known methods for preparing these cyclic ketals.

SUMMARY OF THE INVENTION

Applicants have discovered that certain substituted aromatic compounds, i.e., the substrates of the present invention, can be oxidatively transformed by microbial means to yield 1-substituted cis-2,3-dihydroxy cyclohexa-4,6-diene (referred to herein as "cis-2,3-dihydrodiol") derivatives. These cis-dihydrodiols can be dehydrated chemically to yield meta-substituted phenols which, in turn, can be used to make m-HPA, a key intermediate needed to make AT resins.

The substrates of the present invention are substituted aromatic compounds, e.g., substituted benzenes that are substituted in a manner such that (1) microbial arene-2,3-dioxygenase forms a cis-dihydrodiol at positions 2 and 3 to the substitution, (2) chemical dehydration of the diol results in dehydroxylation at the 2-position, irrespective of the presence of other ring substituents (i.e., to form a "meta-substituted phenol"), and (3) allows chemical conversion at the 1-position to a group containing an ethynyl functionality.

The preferred cis-dihydrodiols of the present invention yield significantly greater amounts of the metahydroxy counterpart than have been described heretofore. For instance, the cis-dihydrodiol obtained from the substrate 2-methyl-2-phenyl-1,3-dioxolane yielded exclusively (i.e., >99%) meta-hydroxyacetophenone instead of the expected ortho-phenol. Similar results were obtained when the substrates were 2-methyl-2-phenyl-4-hydroxymethyl-1,3-dioxolane, and 2-phenyl-1,3-dioxolane. In the latter two cases, the products after dehydration were meta-hydroxyacetophenone and meta-hydroxybenzaldehyde, respectively.

Strains of microorganisms which carry an arene-2,3-dioxygenase enzyme are useful in the invention. Preferably, further oxidative enzymes such as the catechol-producing enzyme (E2 of the above pathway) of the microorganisms is blocked, i.e., genetically or biochemically rendered incapable of oxidizing the dihydrodiol, e.g., converting it to the catechol. Preferably, the strain selected should grow rapidly and have a high tolerance to both the starting substrate and to the cis-2,3-dihydrodiol produced. Good yields and high conversion rates by the strain are also desirable.

Preferred substrates include 2-phenyl-dioxolanes and 2-phenyl-dioxanes which allow growth of the microbial strain in their presence. Substrates of the present invention result in a yield of meta-substituted phenol of at least 10% (by weight, based on the total amount of substituted phenol formed), which is at least double the yield from other known substrates. See, e.g., Gibson, et al., *Biochemistry*, 12(8):1520(1973). Preferably, the yield of the meta-substituted phenol is at least 50%, and most preferably, the yield of meta-substituted phenol is at least 90%. Particularly preferred are substrates that result in a yield of substantially all meta-substituted phenol (i.e., greater than 99%). The word "significant" when used in the context of the dehydroxylation at the 2-position refers to an amount of dehydroxylation at that position corresponding to the above-described yield of meta-substituted phenol.

DESCRIPTION OF THE PREFERRED EMBODIMENTS

The synthesis of m-HPA can be achieved via a combination of biotransformation and chemical synthesis. In the biotransformation step a microorganism is used to transform a suitable aromatic substrate to the corresponding cis-2,3-dihydrodiol, which in turn can be dehydroxylated via dehydration to the meta-substituted derivative. The meta substituent of this phenol allows chemical conversion at the meta position (i.e., at the position of the substituent) to a group containing an ethynyl functionality. Thus, the ability to obtain a phenol substituted at the meta position with a suitable substituent is critical to the success of this route.

The preferred substrates for biotransformation using microbial arene-2,3-dioxygenase are of the following formula:

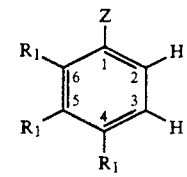

where

Z is a substituent that (1) allows a microbial arene-2,3-dioxygenase to form a cis-dihydrodiol at positions 2 and 3, (2) upon dehydration of the cis-2,3-dihydrodiol, significant dehydroxylation occurs at the 2 position, even when each $R_1$ is H; and (3) allows chemical conversion at the 1-position to a group containing an ethynyl functionality, and where each $R_1$ independently is a non-interfering group, i.e., does not interfere with the aforementioned cis-dihydrodiol formation, the dehydroxylation at the 2-position, or the conversion of the Z group as described above.

Preferably, each $R_1$=H and

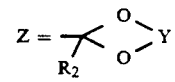

where Y is a $C_2$-$C_3$ alkylene group which may be optionally substituted, e.g., with alkyl (e.g., methyl, ethyl, cyclohexyl) and/or aryl (e.g., phenyl) substituents which, in turn, may be substituted optionally, e.g., by one or more halo groups or hydroxyalkyl, such as —$CH_2OH$, and where $R_2$ is a non-interfering group as to the above described properties of Z. Preferably $R_2$ is —H or —$CH_3$.

Substrates of the present invention can be biotransformed with microbial arene-2,3-dioxygenase to produce cis-2,3-dihydrodiols of the following formula:

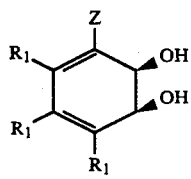

where Y, $R_1$, $R_2$ and Z are as described above. Upon dehydration these cis-2,3-dihydrodiols yield meta-substituted phenols which can then be converted chemically to m-hydroxyphenylacetylene, according to the following general pathway.

Experiments were conducted to use biological methods to produce meta-substituted phenols that are expensive to synthesize chemically and that can be readily converted to m-hydroxyphenylacetylene. It is known, largely from the work of Gibson and colleagues (e.g., Gibson. et al, *Biochemistry* 9:(7):1626(1970)), that some microbes oxidize substituted benzenes with initial attack catalyzed by dioxygenases.

The initial oxygenation is both regio- and enantiospecific to produce a cis-2,3-dihydrodiol as shown above. A strain of *Pseudomonas putida,* designated as strain F39/D, catalyzes the cis-dihydroxylation of a variety of substituted benzenes. Furthermore, this strain is considered "blocked" in that it does not substantially further oxidize the diol. Rather the cis-2,3-dihydrodiol is substantially excreted into the growth medium and can be readily obtained by extraction with ethyl acetate.

The cis-dihydrodiols readily undergo dehydration in the presence of acid to yield phenol(s).

Most cis-2,3-dihydrodiols that have been described rearomatize by loss of the hydroxyl group at the 3-position. Since the objective was to obtain meta-substituted phenols, cis-dihydrodiols that would dehydrate by loss of the hydroxyl at the position adjacent to the substituent were sought. In addition, it was necessary to find substituents that allow chemical conversion to a group containing an ethynyl functionality.

The results are shown in TABLE 1. As can be seen, most of the cis-dihydrodiols undergo dehydration to yield primarily ortho-phenols. Notable exceptions are the cis-dihydrodiols produced by the biotransformation of 2-phenyl-1,3-dioxolane, 2-methyl-2-phenyl-1,3-dioxolane, and 2-methyl-2-phenyl-4-hydroxymethyl-1,3-dioxolane by *Pseudomonas putida* F39/D. Acid treatment of these cis-2,3-dihydrodiols results in dehydroxylation at the 2-position by dehydration, as well as hydrolysis of the dioxolane ring, to produce meta-hydroxyacetophenone or meta-hydroxybenzaldehyde. Hereinafter, the substrates, cis-dihydrodiols, and meta-substituted phenols will be referred to as substrates IA, IIA, IIIA; cis-2,3-dihydrodiols IB, IIB, IIIB; and meta-substituted phenols IC, IIC, and IIIC, respectively.

TABLE 1

| Substrate | Biotransformation Product cis-dihydrodiol | Major Phenols Produced (%) | |
|---|---|---|---|
| [acetophenone] | [cis-dihydrodiol] | [ortho-hydroxyacetophenone] | (95%) |
| [bromobenzene] | [cis-dihydrodiol] | [o-bromophenol] | (95%) |
| [β-chlorostyrene] | [cis-dihydrodiol] | [o-chlorostyrene phenol] | (major) |
| [benzene diol HO OH] | [triol] | [catechol] | (major) |

TABLE 1-continued

| Substrate | Biotransformation Product cis-dihydrodiol | Major Phenols Produced (%) |
|---|---|---|
| IA | IB | IC (99%) |
| IIA | IIB | IIC (99%) |
| IIIA | IIIB | IIIC (99%) |

As shown in TABLE 1, the last three substrates produced significant amounts of a meta-substituted phenol upon dehydration of the corresponding cis-dihydrodiol. It is of interest to note that the cis-dihydrodiol prepared from acetophenone undergoes dehydration to yield largely o-hydroxyacetophenone. The cyclic acetal 2-phenyl-1,3-dioxolane(IA), the cyclic ketal 2-methyl, 2-phenyl-1,3-dioxolane (IIA), and the more water-soluble ketal 2-methyl-2-phenyl-4-hydroxymethyl-1,3-dioxolane (IIIA) each resulted in meta-substituted phenols useful in preparing AT resins.

SURVEY OF SUBSTRATE CHEMICALS

Many microbial strains, such as many of the soil bacteria belonging to the genus Pseudomonas possess biochemical pathways that allow them to metabolize aromatic ring compounds for energy and carbon. One intermediate of this degradative pathway is a cis-2,3-dihydrodiol. These dihydrodiols can be dehydrated to phenols and then converted to the acetylenic phenols chemically. In order to get m-HPA, however, it is first necessary to start with a benzene derivative whose functional group promotes dehydroxylation at the C-2 position upon dehydration and which allows chemical conversion to a group containing an ethynyl functionality.

The major phenol produced by the acid-dehydration of bromobenzene dihydrodiol was an ortho isomer. A detectable amount (5%) of the m-bromophenol was also observed, as shown in TABLE 1.

Two significant parameters of each substrate tested were toxicity and water solubility. The combined effects of those parameters will influence the maximum rate of biotransformation by the microbial culture. Methods were developed to examine the effects of substrate concentration on the rate of biotransformation and cell growth. The rates of biotransformation were apparently independent of the substrates' water solubility. For example, the solubilities of bromobenzene, acetophenone, and 1-phenyl-1,2-ethanediol in MSB buffer (at 30° C.) are approximately 400 mg/liter, 2000 mg/liter, and 5000 mg/liter, respectively. Bromobenzene, one of the least water-soluble substrates tested, was transformed to its dihydrodiol by strain F39/D at an average rate of about 20 mg/liter/hour. The rate of bromobenzene transformation was much greater than that of acetophenone or 1-phenylethanediol transformation, even though the latter compounds are much more water-soluble. Substrate toxicity was determined by examining the growth rate of strain F39/D in the presence of the test compounds. Although the growth of the microbes was apparently unaffected by 400 mg/l (i.e., a saturated level) of bromobenzene, they were completely inhibited by 1000 mg/l (i.e., one-half saturated level) of acetophenone.

ANALYTICAL METHODS

The products obtained from the biotransformation reactions were analyzed by High Pressure Liquid Chromatography ("HPLC"), using a Hewlett Packard HP1090 Liquid Chromatograph (Hewlett Packard, Palo Alto, Calif.) equipped with an HP3388A integrator terminal and a photodiode array detector for spectral analyses in the ultra-violet and visible wavelengths. A reverse-phase octadecylsilane column (Supelco, Inc., Bellefonte, Pa.) was used with aqueous methanol solvent mixtures for HPLC analyses. HPLC chemical standards were of the highest purity available, obtained from Aldrich Chemical Co. (Milwaukee, Wis.).

Thin-layer chromatography ("ITLC") was performed using Whatman type KF-5 silica gel plates (Whatman International Ltd., Maidstone, England) using methyl t-butyl ether as the solvent. Compounds were located on the chromatograms by their ability to quench the fluorescent indicator incorporated into the silica gel.

NMR spectra were obtained from a Varian XL-400 NMR spectrophotometer (Varian Associates, Palo Alto, Calif.) operating at 400 MHz for $^1$H spectra and at 101 MHz for $^{13}$C spectra. Samples undergoing NMR analysis were dissolved in $CDCl_3$.

MICROORGANISMS

Usable microorganisms in this invention include those that possess an arene-2,3-dioxygenase, for example, known Pseudomonas species, Alcaligenes species, and Beijerinckia species. Preferred microorganisms provide an optimal combination of such properties as substrate specificity, substrate and product tolerance, conversion rate, and yield. Presently preferred are the commonly available Pseudomonas putida strains NCIB 11767, NCIB 11680, and F39/D. Genetically altered, e.g., blocked, mutants such as F39/D in which the catechol producing enzymes are absent or rendered inactive are especially useful.

Other suitable methods include the use of isolated arene-2,3-dioxygenase enzymes, e.g., either free in solution or immobilized on a suitable support, according to techniques known to those skilled in the art.

PREPARATION OF STARTING SUBSTRATES

Cyclic acetals and ketals usable as starting substrates can be formed by a general procedure which involves heating an aldehyde or ketone in the presence of a suitable diol, such as ethylene glycol, and an acid catalyst. The water formed from this reaction is removed by azeotropic distillation. All compounds were tested for purity before use and all were found to be of greater than 99% purity by gas chromatography. West German provisional publication 2526312 of Moller et al, published Dec. 30, 1976 provides details on the production of cyclic ketals.

INDUCTION OF MICROORGANISMS

Microorganisms such as many bacteria can be induced to optimize transformation of the substrate to a cis-dihydrodiol. Any accepted method for inducing the cells to synthesize the arene 2,3-dioxygenase enzyme may be employed, e.g., a variety of aromatic compounds may be used.

Optimal conversion by *P. putida* F39/D of aromatic substrates to their corresponding cis-dihydrodiols is facilitated by inducing the cells to synthesize the enzyme, arene-2,3-dioxygenase, with various aromatic compounds. Toluene is the preferred inducing compound. The production of induced cells can accomplished, for example, in the following ways, each of which yields microorganisms capable of oxidizing a variety of aromatic substrates.

1. Induced cells are prepared in 500 ml shake-flask cultures of *P. putida* F39/D by exposing the cell suspension to toluene vapors as described by Spain and Gibson (*Appl. Environ. Microbial.*, 54:1399(1988)).

2. When sample sizes will be less than about 10 liters, the following procedure is preferred. Induced cells are prepared by exposing *P. putida* F39/D cells grown on the surface of MSB medium solidified with agar as described by Gibson et al. (*Biochemistry*, 7:2653(1968)) with the following modifications:

1) The agar medium is contained in 100×15 mm disposable plastic petri dishes (American Scientific Products, McGaw Park, Ill.);

2) The agar medium contains suitable nutrients, such as 3 g/L disodium succinate or 4 g/L L-arginine;

3) The inducing compound is toluene instead of ethylbenzene; and

4) The cells are exposed to the inducing compounds by placing the petri dishes into a chamber containing toluene-saturated air.

The cells are washed off the agar surface with sterile MSB medium, and used in the subsequent biotransformation (oxidation) reaction. This variation is the preferred method because there is no delay in growth when the cells are transferred to the liquid medium containing the aromatic substrates.

BIOTRANSFORMATION

Biotransformation preferably involves the addition of the starting substrate to an induced microbial cell suspension. The microorganisms are then allowed to grow such that the enzyme, arene 2,3-dioxygenase may act on the substrate. The induced microorganisms are prepared as described above. A suspension of the induced cells is immediately transferred to a suitable culture vessel, such as a Multigen F-2000 fermentor (New Brunswick Scientific Co. Edison, N.J.) containing sterile, prewarmed culture medium. The microorganisms are routinely grown at 30 degrees Centigrade in a standard mineral base medium ("MSB") as described by Stanier, et al., *J. General Microbiol.*, 43:159 (1966). The medium is supplemented with suitable nutrients, such as L-arginine hydrochloride (4 g/l) or disodium succinate (3 g/l). The initial cell density in the culture vessel is approximately 25 to 50 g (wet weight) cells per liter MSB medium. The substrate is added to a final concentration of between 0.4 to 10.0 grams per liter MSB medium, depending on its solubility.

The microorganisms are grown in the culture vessel and allowed to oxidize the aromatic substrate for 6 to 18 hours. The cells are then removed from the culture medium by centrifugation or filtration.

EXTRACTION OF DIHYDRODIOLS

The products of the transformation, including the cis-2,3-dihydrodiols, can be extracted by any suitable means, e.g., by ethyl acetate extraction from the culture supernatant as described by Gibson et al. (*Biochemistry*, 12:1520(1973)), the disclosure of which is incorporated herein by reference.

CHEMICAL CONVERSION TO ACETYLENE

The cis-dihydrodiols produced are dehydrated and rearomatized to yield a meta-substituted phenols by any suitable means. Preferably the dehydration is performed by an acid or base catalyzed reaction.

The resulting meta-substituted phenols can be used in any known way to form AT resins. The meta-substituent can be chemically converted to an ethynyl-terminated group by known methods. Suitable methods are described by C. M. Wong and T. L. Ho, "One-step Synthesis of Acetylenes from Ketones," *Synthetic Communications*, 4(1):25–27(1974); *Tetrahedron Letters*, 36:3769 (1972); *J. Organic. Chem.* 34(11):3502–3505 (1969) and *Synthesis*, p. 111 (1973), the disclosures of each of which are incorporated herein by reference.

The meta-hydroxyphenylacetylene so produced may be employed to make AT resins as is well known in the art.

EXAMPLE 1

Cis-2,3-dihydrodiol IIB, as referred to herein, is a 2-(cis-2,3-dihydroxycyclohexa-4,6-dienyl)-2-methyl1,3-dioxolane biotransformed from the ketal, 2-methyl-2-phenyl-1,3-dioxolane (Substrate IIA). It promotes dehydroxylation at the 2-position and will readily yield the meta-substituted phenol (IIC) that, in turn, can be converted chemically to a meta-hydroxyphenylacetylene.

Substrate IIA was prepared by acid-catalyzed ketalization of acetophenone with ethylene glycol. The acid catalyst was p-toluenesulfonic acid and water was removed in an azeotrope with toluene. Substrate IIA was purified by recrystallization in hexane.

*Pseudomonas putida* F39/D (Gibson et al., *Biochemistry* 7(7):2653 (1968)) was grown in a 1 liter flask containing MSB medium supplemented with 4 g/l L-arginine hydrochloride. The flask was incubated at 30° C. shaking on a shaker at 250 rpm.

A 0.2 liter culture of *P. putida* F39/D, having a cell density of 1.1–1.2 absorbance units at 600 nm (approximately 10 g wet weight of cells) was exposed to toluene vapors as described under Method 1 above for inducing cells. After recovery of the induced cells, they were immediately resuspended in fresh growth medium and transferred to a shake flask as described. The volume of prewarmed (30° C.) medium was 0.2 liters. Substrate IIA (0.4 g dissolved in 2 ml dimethyl formamide) was added to the flask. The system was allowed to react in the flask for 6 hours with continuous mixing by shaking as described above.

The cells were removed from the culture liquid by centrifugation at 7600×g. The pH of the culture supernatant was adjusted to 8.4 with 6N sodium hydroxide. The nonionized organic solutes were extracted from the culture fluid with two aliquots of 200 mL of ethyl acetate as described by Gibson et al., (*Biochemistry*, 12:1520 (1973)). After evaporation of the solvent, the product was obtained as a clear oil, which was separated from the starting material by silica gel chromatography.

A 3 cm×8 cm column of silica gel (60–200 mesh, J. T. Baker, Philipsburg, N.J.), in a glass tube was used to separate the dihydrodiols from other materials in the ethyl acetate extracts. The extract (3.0 ml), dissolved in hexane:ethyl acetate (1:1, v/v) was carefully pipetted onto the top of the silica gel. The column was then washed with five column volumes (approximately 200 ml) of a mixture (1:1) of hexane:ethyl acetate. The cis-dihydrodiol (IIB) was then eluted from the column in 100% ethyl acetate. Five-milliliter (5 ml) fractions were collected from the column and fractions containing the dihydrodiol were identified by TLC.

The product, eluted with ethyl acetate, was initially analyzed by reverse-phase HPLC, and was tentatively identified as a dihydrodiol on the basis of its HPLC elution characteristics and by its ultra-violet absorption spectrum. The material was further analyzed by NMR spectroscopy and was found to consist of the dihydrodiols derived from acetophenone and 2-methyl-2-phenyl-1,3-dioxolane (Substrate IIA), which comprised 20% and 80%, respectively, of the products recovered.

The extracted cis-dihydrodiols, which contained little or no water, were dissolved in $CDCl_3$ and adjusted to 0.1N HCl by adding concentrated (12N) aqueous HCl. The dehydration reaction was allowed to proceed at about 80° C. for at least 30 minutes or at about 23° C. for 4 to 24 hours.

This yielded a mixture of phenols in the proportion of 20% 2-hydroxyacetophenone and 80% 3-hydroxyacetophenone (meta-substituted phenol IIC), respectively, identified by NMR spectroscopy. When compound IIB was purified to homogeneity by TLC and was hydrolyzed in chloroform with HCl, the exclusive phenol was meta-hydroxy acetophenone (IIC), identified by NMR.

EXAMPLE 2

Substrate IA, 2-phenyl-1,3-dioxolane, was prepared by acid-catalyzed acetalization of benzaldehyde with ethylene glycol. The acid catalyst was methane-sulfonic acid and water was removed in an azeotrope with cyclohexane, and the product was purified by fractional distillation.

The substrate was biotransformed by *P. putida*, and the products analyzed, according to the methods described in EXAMPLE 1. The exclusive phenol produced was meta-hydroxy benzaldehyde.

EXAMPLE 3

Substrate IIIA, 2-methyl-2-phenyl-4-hydroxymethyl-1,3-dioxolane, was prepared similarly to Substrate IIA except that glycerol was used in place of ethylene glycol, and the product was purified by fractional distillation.

The substrate was biotransformed by *P. putida*, and the products analyzed, according to the methods described in EXAMPLE 1. The exclusive phenol produced was meta-hydroxy acetophenone.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiments described herein which equivalents are intended to be encompassed by the claims attached hereto.

What is claimed is:

1. A method for making a meta-substituted phenol of the formula

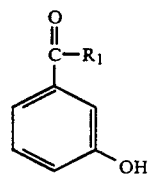

comprising the steps of:

(a) biotransforming a substrate of the formula

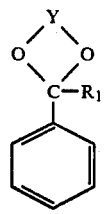

wherein R₁ is hydrogen or methyl and Y is —CH₂CH₂—, CH₂CH₂CH₂— or —CH(CH₂OH)—CH₂— with an arene-2,3-dioxygenase enzyme to form a cis -2,3-dihydrodiol of the formula

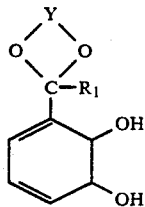

and (b) dehydrating the cis-2,3-dihydrodiol in the presence of acid to form the meta-substituted phenol in a yield of about 95 wt % or more.

2. A method according to claim 1 wherein the yield of meta-substituted phenol is about 99 wt % or more.

3. The method according to claim 1 wherein the substrate is 2-phenyl-1,3-dioxolane.

4. The method according to claim 1 wherein the substrate is 2-methyl-2-phenyl-1,3-dioxolane.

5. The method according to claim 1 wherein the substrate is 2-methyl-2-phenyl-4-hydroxy methyl-1,3-dioxolane.

6. A method for the preparation of a cis-2,3, dihydrodiol of the formula

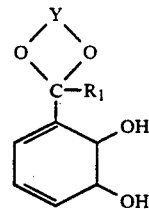

comprising the step of biotransforming a substrate of the formula

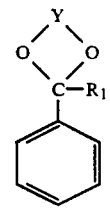

wherein R₁ is hydrogen or methyl and Y is —CH₂CH₂—, CH₂CH₂CH₂— or —CH(CH₂OH)—CH₂— with an arene-2,3-dioxygenase enzyme to form the cis-2,3-dihydrodiol.

7. The method according to claim 6 wherein the substrate is 2-methyl-2-phenyl-1,3-dioxolane.

8. The method according to claim 6 wherein the substrate is 2-phenyl-1,3-dioxolane.

9. The method according to claim 6 wherein the substrate is 2-methyl-2-phenyl-4-hydroxymethyl-1,3-dioxolane.

* * * * *